(12) United States Patent
Kanyuh

(10) Patent No.: US 8,044,254 B2
(45) Date of Patent: Oct. 25, 2011

(54) PROCESS FOR ENHANCED OLEFIN PRODUCTION

(75) Inventor: Adam J. Kanyuh, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 190 days.

(21) Appl. No.: 12/404,845

(22) Filed: Mar. 16, 2009

(65) Prior Publication Data

US 2009/0178954 A1 Jul. 16, 2009

(51) Int. Cl.
*C07C 4/02* (2006.01)
(52) U.S. Cl. ........ 585/648; 585/638; 585/639; 585/650; 585/651; 585/652; 585/910; 208/106; 208/113; 208/125; 208/128; 208/130
(58) Field of Classification Search .................. 585/638, 585/639, 648, 650, 652, 651, 910; 208/106, 208/125, 128, 130, 113; 422/198, 200, 207
See application file for complete search history.

(56) References Cited

U.S. PATENT DOCUMENTS

| | | | | |
|---|---|---|---|---|
| 5,849,979 A | * | 12/1998 | Kalnes et al. | 585/809 |
| 6,013,852 A | * | 1/2000 | Chandrasekharan et al. | 585/648 |
| 6,121,504 A | * | 9/2000 | Kuechler et al. | 585/640 |
| 6,294,079 B1 | | 9/2001 | Thakkar et al. | |
| 6,294,080 B1 | | 9/2001 | Thakkar et al. | |
| 6,403,854 B1 | * | 6/2002 | Miller et al. | 585/638 |
| 6,459,009 B1 | | 10/2002 | Miller et al. | |
| 7,011,740 B2 | * | 3/2006 | Tallman et al. | 208/113 |
| 7,038,102 B2 | | 5/2006 | Van Egmond et al. | |
| 7,317,133 B2 | | 1/2008 | Vora et al. | |
| 7,329,790 B2 | | 2/2008 | Bjorklund et al. | |

FOREIGN PATENT DOCUMENTS

| | | |
|---|---|---|
| JP | 61171436 | 8/1986 |
| JP | 61176692 | 8/1986 |

OTHER PUBLICATIONS

Fair, et al., "Gas Absorption and Gas-Liquid System Design" in Perry's Chemical Engineers Handbook, 7th ed., R. H. Perry and D. W. Green, ed., 1997, McGraw-Hill, available on-line at www.knovel.com.*
Barker, et al., "Petroleum" in Kirk-Othmer Encyclopedia of Chemical Technology, J. Wiley & Sons, available on-line May 13, 2005.*
Shilling, et al., "Heat Transfer Equipment" in Perry's Chemical Engineers Handbook, 7th ed., R. H. Perry and D. W. Green, ed., 1997, McGraw-Hill, available on-line at www.knovel.com.*

* cited by examiner

*Primary Examiner* — In Suk Bullock
*Assistant Examiner* — Bradley Etherton
(74) *Attorney, Agent, or Firm* — Arthur E. Gooding

(57) ABSTRACT

A processing scheme and arrangement for enhanced olefin production involves cooling or treating an olefin cracking reactor effluent stream by contacting the olefin cracking reactor effluent stream with a quench oil stream in a single contact cooler contact zone to produce a cooled vapor stream and to form a heated quench oil stream. A pressure differential across the single contact cooler is less than about 3.5 kPa. The heated quench oil stream can be subsequently cooled and returned to the single contact cooler.

18 Claims, 2 Drawing Sheets

PROCESS FOR ENHANCED OLEFIN PRODUCTION

FIELD OF THE INVENTION

The invention relates generally to the production of light olefins and, more particularly, to the production of light olefins via the cracking of heavier olefins.

BACKGROUND OF THE INVENTION

A major portion of the worldwide petrochemical industry is concerned with the production of light olefin materials and their subsequent use in the production of numerous important chemical products via polymerization, oligomerization, alkylation and other well-known chemical reactions. Light olefins include ethylene, propylene and mixtures thereof. These light olefins are essential building blocks for the modern petrochemical and chemical industries.

Olefin conversion technologies may be employed to produce light olefins from other olefins. Such olefin conversion processes are often combined or integrated with other olefin producing technologies such as, for example, steam or fluid catalytic cracking processes or oxygenate to olefin processes to provide increased light olefin production.

There are generally two main types of olefin conversion technologies available to produce light olefins, metathesis and olefin cracking. Such metathesis processes typically produce propylene by reacting ethylene with 2-butenes. Such olefin cracking processes typically produce ethylene and propylene by cracking or converting $C_4$-$C_8$ feedstocks to produce effluent streams containing predominantly $C_2$-$C_6$ compounds along with some hydrogen and other lighter gases. Such effluent streams are subsequently separated into various product streams such as, for example, product streams containing ethylene and propylene.

While such processing can desirably result in the formation of increased relative amounts of propylene and/or ethylene, further improvements such as to further enhance the relative amount of propylene and/or ethylene production and recovery are desired and have been sought.

Generally, olefin cracking processes are conducted in a reactor at elevated temperatures and typically produce effluent streams having temperatures in excess of 500° C. Such olefin cracking reactor effluent streams are subsequently cooled and compressed to facilitate separation into individual product streams. Olefin cracking reactor effluent streams can be cooled using various heat exchange methods such as, for example, indirect heat exchange with a cooling medium such as, for example, cooling water. One such indirect heat exchange method generally involves passing the hot olefin cracking reactor effluent through a heat exchange unit such as, for example, a tube and shell heat exchanger, to produce a cooled olefin cracking reactor effluent stream having a temperature profile that is suitable for efficient compression.

However, such indirect heat exchange units can be susceptible to fouling by constituents of the olefin cracking reactor effluent stream. For example, heavy hydrocarbon compounds can condense on surfaces of the heat exchange unit which can result in a reduction of the cooling capacity of the heat exchange unit. Generally, the temperature of a gas to be compressed controls the capacity of an associated compressor, i.e., the higher the temperature of the gas the less it can be compressed. Thus, reducing the cooling capacity of the heat exchange unit results in a reduced compression capacity in an associated compressor which can, in turn, result in increased down time for cleaning of the heat exchange units and decreased product output.

In view of the above, there is a need and a demand for processing schemes and/or arrangements effective to reduce fouling of heat exchange units used to cool olefin cracking reactor effluent streams.

Additionally, gaseous materials which pass through such indirect heat exchange units can also experience a significant pressure drop from inlet to outlet resulting in a cooled effluent stream having a pressure which is lower than may be desired and can require additional energy expenditures and increased compressor size to compress the cooled effluent stream to a pressure suitable for further processing in subsequent separation units. Thus, there is a further need and a demand for processing schemes and/or arrangements that result in a reduced pressure drop across the heat exchange unit.

Further, a pressure drop across the heat exchange unit can result in an increased pressure at an associated olefin cracking reactor outlet which can cause reductions in the yield of ethylene and/or propylene produced by the olefin cracking process. Accordingly, there is a still further need and a demand for processing schemes and/or arrangements effective to result in an increased relative yield of light olefins, particularly, ethylene and/or propylene.

SUMMARY OF THE INVENTION

A general objective of the invention is to provide an improved process and system for producing an increased yield of light olefins from an olefin-rich feedstock stream.

A more specific objective of the invention is to overcome one or more of the problems described above.

The general object of the invention can be attained, at least in part, through a process for cooling an olefin cracking reactor effluent stream involving contacting the olefin cracking reactor effluent stream with a quench oil stream in a single contact cooler contact zone to produce a cooled vapor stream and to form a heated quench oil stream, with a pressure drop from an inlet of the contact cooler to an outlet of the contact cooler of less than about 3.5 kPa (about 0.5 psi). The process can additionally involve cooling the heated quench oil stream and returning a portion of the cooled oil stream to the contact cooler.

The prior art generally fails to provide processing schemes and arrangements that are as effective as desired in increasing the relative yield of light olefins compared to conventional olefin cracking and recovery processes. Further, the prior art generally fails to provide processing schemes and arrangements that result in desirably reduced fouling and/or pressure drop across associated heat exchange units.

In accordance with another embodiment, a process for treating an olefin cracking reactor effluent stream involves cooling the olefin cracking reactor effluent stream via indirect heat exchange with a reactor feed stream in a first heat exchange zone to produce a cooled effluent stream having a temperature in a range of about 150° C. to about 210° C. The process further involves contacting the cooled effluent stream with a quench oil stream in a single packed bed contact cooler contact zone to produce a cooled vapor stream having a temperature in a range of about 25° C. to about 55° C. and to form a heated oil stream. The heated oil stream is combined with a heavy oil feed stream to produce a combined heavy oil stream. At least a first portion of the combined heavy oil stream is returned to the cooling cooler to provide the quench oil stream.

In accordance with yet another embodiment, a process for producing an increased yield of light olefins from an olefin-rich feedstock stream involves introducing the olefin-rich feedstock stream comprising $C_4$ to $C_8+$ olefins to an olefin cracking reactor to produce an effluent stream including at least one of ethylene and propylene. The effluent stream is cooled via indirect heat exchange with the olefin-rich feedstock stream in a first heat exchange zone to produce a cooled effluent stream. The cooled effluent stream is contacted with a quench oil stream in a single packed bed contact cooler contact zone to produce a cooled vapor stream and to form a heated quench oil stream, with a pressure differential from an effluent stream inlet to a cooled vapor stream outlet of the contact cooler of less than about 3.5 kPa (about 0.5 psi).

The cooled vapor stream is separated into at least one light weight stream including a light olefin selected from ethylene, propylene and combinations thereof. The heated quench oil stream is combined with a heavy oil stream to produce a combined heavy oil stream. The combined heavy oil stream is cooled via indirect heat exchange with a cooling medium stream in a second heat exchange zone to produce a cooled oil stream. A first portion of the cooled oil stream is returned to the single packed bed contact cooler to provide the quench oil stream.

A system for producing ethylene and propylene is also provided. The system includes an olefin cracking reactor for converting at least a portion of a $C_4+$ olefin-rich feedstock stream into an olefin cracking reactor effluent stream including at least one of ethylene and propylene. The system further includes a single bed contact cooler wherein at least a portion of the olefin cracking reactor effluent stream contacts a quench oil stream in a contact zone to produce a cooled vapor stream and to form a heated quench oil stream. The contact cooler has a pressure differential from an olefin cracking reactor effluent stream inlet to a cooled vapor stream outlet of less than about 3.5 kPa (less than about 0.5 psi). The system also includes a heat exchanger wherein the heated quench oil stream is cooled via indirect heat exchange with a cooling medium stream to form a cooled oil stream As used herein, references to "light olefins" are to be understood to generally refer to $C_2$ and $C_3$ olefins, i.e., ethylene and propylene.

Other objects and advantages will be apparent to those skilled in the art from the following detailed description taken in conjunction with the appended claims and drawings.

DETAILED DESCRIPTION OF THE INVENTION

A $C_4+$ olefin-rich feedstock stream can be cracked in a reactor to produce a olefin cracking reactor effluent stream comprising a range of hydrocarbon products including $C_2$ and/or $C_3$ olefins, unconverted $C_4$ to $C_8+$ hydrocarbons, and aromatic hydrocarbons such as, for example, benzene and toluene, as well as some hydrogen and other light gases such as, for example, methane, ethane and/or propane. At least a portion of such olefin cracking reactor effluent stream can be subsequently cooled and separated to recover ethylene and/or propylene.

Figure 1:
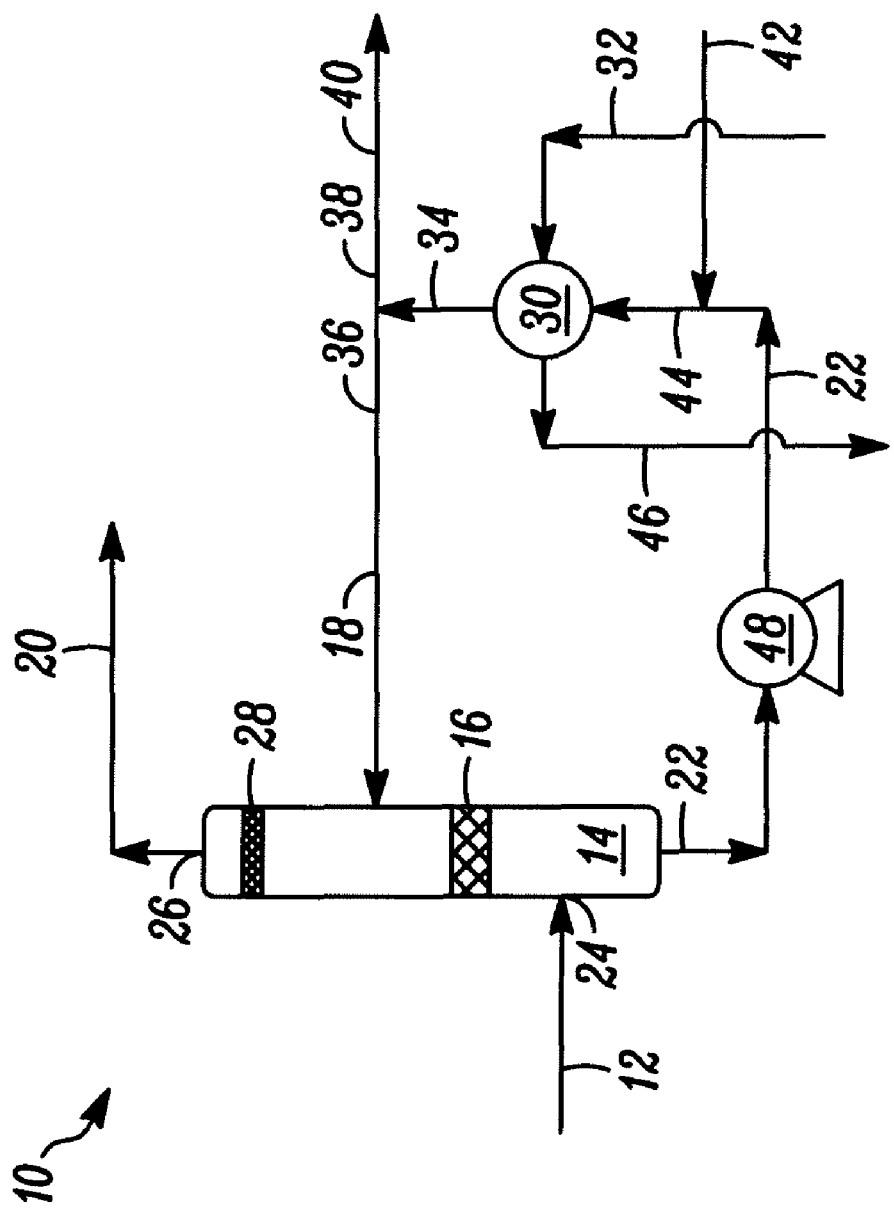
FIG. 1 is a simplified schematic diagram of a process for cooling an olefin cracking reactor effluent stream in accordance with one embodiment.

FIG. 1 schematically illustrates a system, generally designated by the reference numeral 10, for cooling an olefin cracking reactor effluent stream to produce or result in an increased relative amount of light olefins in accordance with one embodiment.

More particularly, in the system 10, an olefin cracking reactor effluent stream 12 is introduced into a contact cooler 14 below a single contact zone 16. A quench oil stream 18 is introduced into the contact cooler 14 above the single contact zone 16. The cracking reactor effluent stream 12 contacts the quench oil stream 18 in the single contact zone 16 in a countercurrent manner to produce a cooled vapor stream 20 and a heated quench oil stream 22. Materials passing through the contact cooler 14 from an olefin cracking effluent steam inlet 24 to a cooled vapor stream outlet 26 have a pressure drop of less than about 3.5 kPa (about 0.5 psi).

In accordance with certain embodiments, the olefin cracking reactor effluent stream 12 may be introduced into the contact cooler 14 at a pressure of about 7 to about 21 kPa gauge (about 1 to about 3 psig).

The olefin cracking reactor effluent stream 12 can desirably have a temperature in a range of about 120° C. to about 210° C. (about 250° F. to about 400° F.) and can be cooled via contact with the quench oil stream 18 in the contact zone 16 to produce the cooled vapor stream 20 having a temperature in a range of about 25° C. to about 55° C. (about 75° F. to about 130° F.). In accordance with certain embodiments, the olefin cracking reactor effluent stream 12 can have a temperature in a range of about 150° C. to about 210° C. (about 300° F. to about 400° F.) and can be cooled via contact with the quench oil stream 18 to produce a cooled vapor stream 20 having a temperature in a range of about 35° C. to about 45° C. (about 95° F. to about 115° F.).

In accordance with certain embodiments, the cooled vapor stream 20 can be subsequently separated into at least one light weight stream including a light olefin selected from ethylene, propylene and combinations thereof.

The quench oil stream 18 can desirably have a temperature in a range of about 20° C. to about 40° C. (about 70° F. to about 100° F.) and can be heated via contact with the olefin cracking reactor effluent stream 12 in the contact zone to form the heated quench oil stream 22 having a temperature in a range of about 50° C. to about 75° C. (about 120° F. to about 165° F.). In accordance with certain embodiments, the quench oil stream 18 can have a temperature in a range of about 30° C. to about 35° C. (about 85° F. to about 95° F.). In accordance with certain other embodiments, the quench oil stream 18 can be heated via contact with the olefin cracking reactor effluent stream 12 to form the heated quench oil stream 22 having a temperature in a range of about 55° C. to about 65° C. (about 130° F. to about 150° F.).

In accordance with certain embodiments, the single contact zone 16 may be a single packed bed containing an inert packing material. Various suitable packing materials known in the art, such as, for example, rasching rings, can be employed in the packed bed. In accordance with certain other embodiments, the single contact zone 16 can include a tray assembly and/or may be a combination of a packed bed and a tray assembly such as, for example, rasching rings followed by a disk and doughnut tray assembly.

Prior to exiting the contact cooler 14 the cooled vapor stream 20 suitably passes through a mesh blanket or wire scrubber 28 wherein liquid droplets containing condensed hydrocarbons such as, for example, $C_6+$ hydrocarbons and/or aromatic compounds such as, for example, benzene and toluene, are removed from the cooled vapor stream 20. Such condensed liquid droplets are suitably absorbed by the quench oil stream 18 and are removed from the contact cooler 14 via the heated quench oil stream 22. Such mesh blanket or wire scrubber 28 may be constructed of tightly wrapped wires composed of an inert and/or corrosion-resistant material such as, for example, 316 stainless steel.

In addition to the condensed liquid droplets, the quench oil stream 18 may absorb or otherwise extract heavy components such as, for example, $C_6+$ hydrocarbons and/or aromatic compounds such as, for example, benzene and toluene, from the olefin cracking reactor effluent stream 12 via physical contact of the olefin cracking reactor effluent stream 12 with the quench oil stream 18 in the contact zone 16. Such heavy components are removed from the contact zone 16 via the heated quench oil stream 22.

The quench oil stream 18 advantageously includes at least one $C_{10}+$ hydrocarbon material. The use of such $C_{10}+$ hydrocarbon materials is desirable to minimize and/or otherwise prevent vaporization of the quench oil material into the cooled vapor stream 20. In accordance with certain embodiments, the quench oil stream 18 advantageously includes kerosene.

The system 10 can further include a first heat exchange zone 30 wherein the heated quench oil stream 22 is cooled via indirect heat exchange with a cooling medium stream 32 to produce a cooled oil stream 34 and a heated cooling medium stream 46. Suitably, the heated quench oil stream 22 can be cooled via indirect heat exchange with the cooling medium stream 32 to produce the cooled oil stream 34 having a temperature in a range of about 20° C. to about 40° C. (about 70° F. to about 100° F.). In accordance with certain embodiments, the cooled oil stream 34 can have a temperature in a range of about 35° C. to about 40° C. (about 95° F. to about 100° F.). At least a first portion 36 of the cooled oil stream 34 may be returned to the contact cooler 14 to provide the quench oil stream 18.

A second portion 38 of the cooled effluent stream 34 can be removed from or drawn off the system 10 to produce a drag oil stream 40. Such drag oil stream 40 is advantageously drawn off or removed from the system 10 to reduce or eliminate the build-up of heavy hydrocarbons such as, for example, $C_6+$ hydrocarbons and/or aromatic hydrocarbons such as, for example, benzene and toluene, which are absorbed or extracted from the olefin cracking reactor effluent stream 12 by the quench oil stream 18 in contact zone 16. Drawing off such drag oil stream 40 can also prevent build-up or condensation of heavy hydrocarbons within the system 10.

In accordance with certain embodiments, the heated quench oil stream 22 may be combined with a heavy oil stream 42 to produce a combined heavy oil stream 44. Such combined heavy oil stream 44 can be subsequently cooled via indirect heat exchange with the cooling medium stream 32 in the first heat exchange zone 30 to produce the cooling oil stream 34 having a temperature in a range of about 20° C. to about 40° C. (about 70° F. to about 100° F.).

The heavy oil stream 42 advantageously includes at least one $C_{10}+$ hydrocarbon material. The use of such $C_{10}+$ hydrocarbon material is desirable to minimize and/or otherwise prevent vaporization of the quench oil material into the cooled vapor stream 20. In accordance with certain embodiments, the heavy oil stream 42 advantageously includes kerosene.

In accordance with certain embodiments the cooling medium stream 32 can include a cooling water stream or an air cooling stream. The cooling medium stream 32 can suitably have a temperature of less than about 35° C. (about 95° F.). In practice, the cooling medium stream 32 is heated via indirect heat exchange with heated quench oil stream 22 or, in accordance with certain embodiments, with the combined heavy oil stream 44, to form the heated cooling medium stream 46.

In accordance with certain additional embodiments, the system 10 may further include a pump 48 for recycling the heated quench oil stream 22 or, in accordance with certain embodiments (not shown), the combined heavy oil stream 44, through the first heat exchange zone 30 to produce the cooled oil stream 34, the quench oil stream 18 and the drag oil stream 40.

Figure 2:
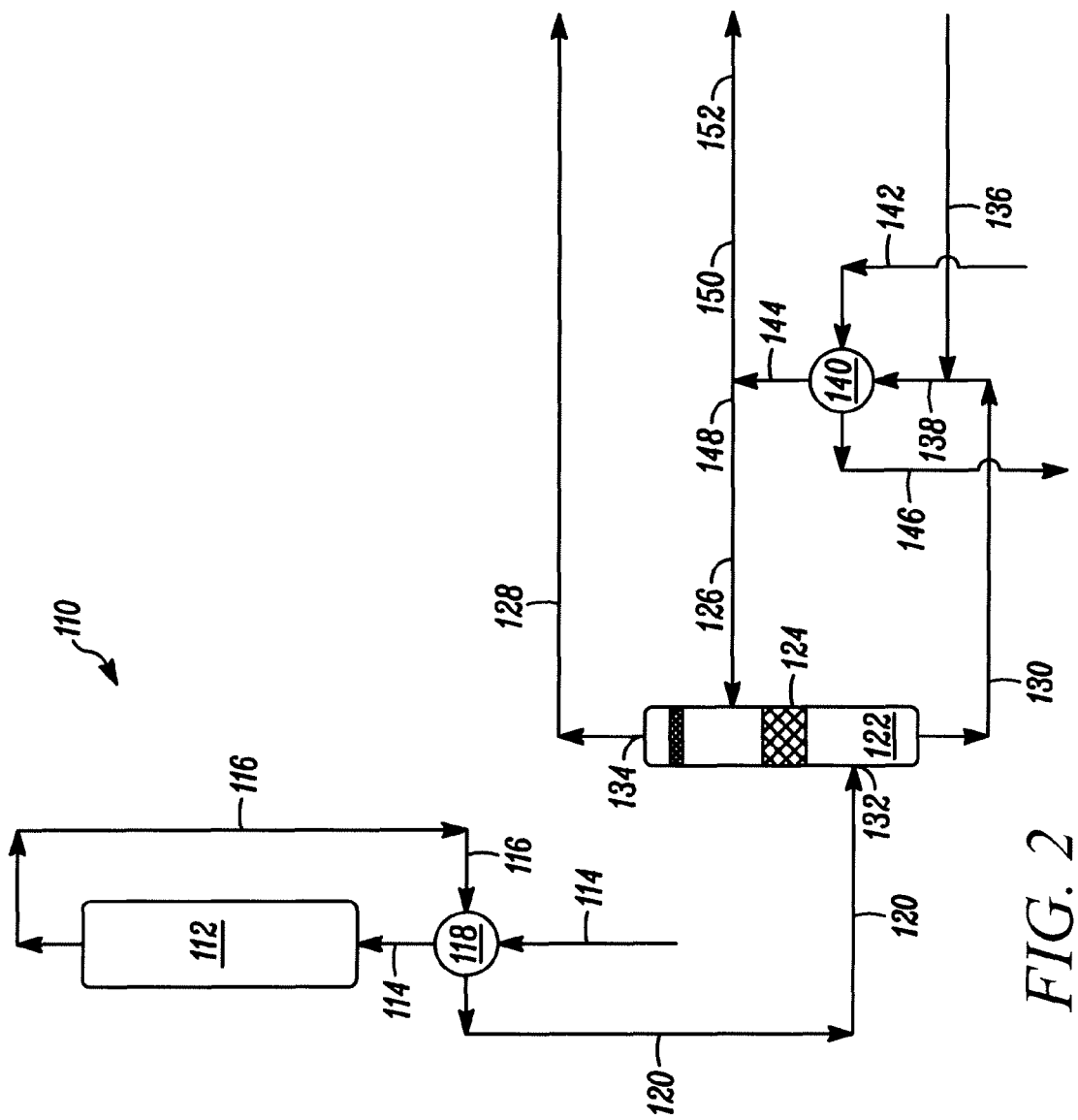
FIG. 2 is a simplified schematic diagram of a process for treating an olefin cracking reactor effluent stream in accordance with another embodiment.

In accordance with certain further embodiments, as illustrated in FIG. 2, a system, generally designated by reference numeral 110, for treating an olefin cracking reactor effluent stream, includes an olefin cracking reactor 112 wherein an olefin-rich feedstock stream 114 including $C_4$ to $C_8+$ olefins is cracked to produce a olefin cracking reactor effluent stream 116 including at least one of ethylene and propylene.

In accordance with certain embodiments the olefin-rich feedstock stream 114 may include an effluent stream selected from steam cracking effluent streams, fluidized catalytic cracking effluent streams and oxygenate to olefin reactor effluent streams.

The system 110 further includes a first heat exchange zone 118 wherein the olefin cracking reactor effluent stream 116 is cooled via indirect heat exchange with the olefin-rich feedstock stream 114 to produce a cooled effluent stream 120.

In accordance with certain embodiments the olefin cracking reactor effluent stream 116 having a temperature in a range of about 500° C. to about 600° C. (about 930° F. to about 1110° F.) is cooled via indirect heat exchange with the olefin-rich feedstock stream 114 in the first heat exchange zone 118 to produce the cooled effluent stream 120 having a temperature in a range of about 120° C. to about 210° C. (about 250° F. to about 400° F.). In accordance with certain other embodiments the olefin cracking reactor effluent stream 116 is cooled in the first heat exchange zone 118 to produce the cooled effluent stream 120 having a temperature in a range of about 150° C. to about 210° C. (about 300° F. to about 400° F.).

The cooled effluent stream 120 is introduced into a contact cooler 122 below a single contact zone 124. A quench oil stream 126 is introduced into the contact cooler 122 above the single contact zone 124. The cooled effluent stream 120 contacts the quench oil stream 126 in the single contact zone 124 in a countercurrent manner to produce a cooled vapor stream 128 and heated quench oil stream 130. In accordance with certain embodiments materials passing through the contact cooler 122 from a cooled effluent steam inlet 132 to a cooled vapor stream outlet 134 have a pressure drop of less than about 3.5 kPa (about 0.5 psi).

In accordance with certain embodiments, the single contact zone 124 can be a single packed bed containing an inert packing material or a tray assembly such as described above.

The heated quench oil stream 130 is subsequently combined with a heavy oil feed stream 136 to produce a combined heavy oil stream 138. In accordance with certain embodiments at least a first portion of the combined heavy oil stream 138 is returned the contact cooler 122 to provide the quench oil stream 126.

Advantageously, the combined heavy oil stream 138 is cooled in a second heat exchange zone 140 via indirect heat exchange with a cooling medium stream 142 to produce a cooled oil stream 144 and heated cooling medium stream 146. A first portion 148 of the cooled oil stream 144 is returned to the contact cooler 122 to provide the quench oil stream and a second portion 150 of the cooled oil stream 144 is drawn off to form a drag oil stream 152.

Embodiments, such as described above, desirably provide or result in improved processing of olefin cracking reactor effluent streams to produce an increased relative yield of light olefins and which processing is desirably more effective and/or efficient than heretofore reasonably possible via conventional olefin cracking processing and associated product separation processes. More specifically, such embodiments, through cooling of olefin cracking reactor effluent streams via direct contact with a quench oil stream, can improve processing economics. For example, such processing can desirably minimize system fouling by heavy hydrocarbons and reduce differential pressure losses during cooling and recovery processes.

The invention illustratively disclosed herein suitably may be practiced in the absence of any element, part, step, component or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A process for cooling an olefin cracking reactor effluent stream, the process comprising:
    producing the olefin cracking reactor effluent stream in an olefin cracking reactor, wherein the olefin cracking reactor effluent stream comprises $C_2$ to $C_3$ olefins;
    contacting the olefin cracking reactor effluent stream with a quench oil stream in a single contact cooler contact zone to produce a cooled vapor stream and to form a heated quench oil stream;
    maintaining the olefin cracking reactor effluent stream at a pressure of about 7 kPa gauge to about 21 kPa gauge at an inlet of the contact cooler to increase a yield of the $C_2$ to $C_3$ olefins in the olefin cracking reactor effluent stream; and
    limiting a pressure difference between the inlet of the contact cooler and an outlet of the contact cooler to less than about 3.5 kPa.

2. The process of claim 1 additionally comprising:
    cooling the heated quench oil stream via indirect heat exchange with a cooling medium stream in a first heat exchange zone to produce a cooled oil stream;
    returning a first portion of the cooled oil stream to the contact cooler to provide the quench oil stream; and
    drawing off a second portion of the cooled oil stream to produce a drag oil stream.

3. The process of claim 2 additionally comprising:
    before cooling the heated quench oil stream, combining a heavy oil feed stream with the heated quench oil stream.

4. The process of claim 1 further comprising:
    cooling all of the heated quench oil stream formed from contacting the olefin cracking reactor effluent stream with the quench oil stream in the single contact cooler contact zone via indirect heat exchange with a cooling medium stream in a first heat exchange zone to produce a cooled oil stream.

5. The process of claim 4 further comprising:
    before cooling all of the heated quench oil stream, combining a heavy oil feed stream with the heated quench oil stream.

6. The process of claim 5 further comprising:
    returning a first portion of the cooled oil stream to the contact cooler to provide the quench oil stream; and
    drawing off a second portion of the cooled oil stream to produce a drag oil stream.

7. The process of claim 1 wherein the quench oil comprises at least one $C_{10}$+ hydrocarbon.

8. The process of claim 1 additionally comprising:
    separating the cooled vapor stream into at least one light weight stream comprising a light olefin selected from the group consisting of ethylene, propylene and combinations thereof.

9. A process for treating an olefin cracking reactor effluent stream, the process comprising:
    producing the olefin cracking reactor effluent stream in an olefin cracking reactor, wherein the olefin cracking reactor effluent stream comprises $C_2$ to $C_3$ olefins;
    cooling the olefin cracking reactor effluent stream via indirect heat exchange with a reactor feed stream in a first heat exchange zone to produce a cooled effluent stream having a temperature in a range of about 150° C. to about 210° C.;
    contacting the cooled effluent stream with a quench oil stream in a single packed bed contact cooler contact zone to produce a cooled vapor stream having a temperature in a range of about 25° C. to about 55° C. and to form a heated oil stream, wherein the cooled effluent stream is
    maintained at a pressure of about 7 kPa gauge to about 21 kPa gauge at an inlet of the contact cooler to increase a yield of the $C_2$ to $C_3$ olefins in the olefin cracking reactor effluent stream;
    combining the heated oil stream with a heavy oil feed stream to produce a combined heavy oil stream; and
    returning a first portion of the combined heavy oil stream to the contact cooler to provide the quench oil stream.

10. The process of claim 9 additionally comprising:
    cooling the combined heavy oil stream via indirect heat exchange with a cooling medium in a second heat exchange zone.

11. The process of claim 10 wherein all of the heated oil stream formed by contacting the cooled effluent stream with a quench oil stream in a single packed bed contact cooler contact zone is combined with the heavy oil feed stream.

12. The process of claim 9 wherein the quench oil stream has a temperature in a range of about 20° C. to about 40° C.

13. The process of claim 11 additionally comprising:
    drawing off a second portion of the combined heavy oil stream to produce a drag oil stream.

14. A process for producing an increased yield of light olefins from an olefin-rich feedstock stream, the process comprising:
    introducing the olefin-rich feedstock stream comprising $C_4$ to $C_8$+ olefins to an olefin cracking reactor to produce an effluent stream comprising at least one of ethylene and propylene;
    cooling the effluent stream via indirect heat exchange with the olefin-rich feedstock stream in a first heat exchange zone to produce a cooled effluent stream;
    contacting the cooled effluent stream with a quench oil stream in a single packed bed contact cooler contact zone to produce a cooled vapor stream and to form a heated quench oil
    wherein the cooled effluent stream is maintained at a pressure of about 7 kPa gauge to about 21 kPa gauge at an inlet of the contact cooler contact zone to increase a reactor yield of the at least one of ethylene and propylene in the effluent stream produced by the olefin cracking reactor, and wherein a pressure difference between an effluent stream inlet of the contact cooler and a cooled vapor stream outlet of the single packed bed contact cooler is limited to less than about 3.5 kPa;

separating the cooled vapor stream into at least one light weight stream comprising a light olefin selected from the group consisting of ethylene, propylene and combinations thereof;

combining the heated oil stream with a heavy oil feed stream to produce a combined heavy oil stream;

cooling the combined heavy oil stream via indirect heat exchange with a cooling medium stream in a second heat exchange zone to produce a cooled combined oil stream; and returning a first portion of the cooled combined oil stream to the single packed bed contact cooler to provide the quench oil stream.

15. The process of claim 14 wherein all of the heated oil stream is combined with the heavy oil feed stream to produce the combined heavy oil stream.

16. The process of claim 15 additionally comprising:
drawing off a second portion of the cooled combined oil stream to produce a drag oil stream comprising a compound selected from the group consisting of heavy hydrocarbons, aromatic compounds and combinations thereof.

17. The process of claim 14 additionally comprising:
drawing off a second portion of the cooled combined oil stream to produce a drag oil stream comprising a compound selected from the group consisting of heavy hydrocarbons, aromatic compounds and combinations thereof.

18. The process of claim 14 wherein the cooling medium stream comprises cooling water.

* * * * *